US00PP09696P

United States Patent [19]

Fear

[11] Patent Number: Plant 9,696

[45] Date of Patent: Nov. 19, 1996

[54] RASPBERRY PLANT CV. 'GODIVA'

[75] Inventor: Carlos D. Fear, Aptos, Calif.

[73] Assignee: Sweetbriar Development, Inc., Watsonville, Calif.

[21] Appl. No.: 430,538

[22] Filed: Apr. 25, 1995

[51] Int. Cl.[6] ..... A01H 5/00

[52] U.S. Cl. ..... Plt./46.2

[58] Field of Search ..... Plt./46.2

*Primary Examiner*—James R. Feyrer

*Attorney, Agent, or Firm*—Synnestvedt & Lechner

[57] ABSTRACT

A new and distinct cultivar of yellow raspberry plant named 'Godiva', which is particularly characterized and distinguished by its fruit of excellent flavor and yellow color and its high yielding capacity on both primocane and floricane crops.

3 Drawing Sheets

BACKGROUND AND SUMMARY OF THE INVENTION

This invention relates to a new and distinct cultivar of raspberry plant that has been given the cultivar name or denomination 'Godiva'. The new cultivar was developed from hydridization of the selection C96.7 (an unpatented proprietary cultivar) as the seed parent with the selection F167.1 (an unpatented proprietary cultivar) as the pollen parent. The parents were crossed by Carlos Fear in June 1989, whereafter fruit and seed were collected to produce seedlings for field planting in Watsonville, Calif. in January 1990. The new cultivar was selected from these seedlings by Carlos Fear in October 1990 for its distinguishing fruit firmness, good flavor and distinguishing yellow color. Since its selection, the 'Godiva' cultivar has been asexually propagated by in vitro shoot tip culture, root sucker division and root cuttings, and has been shown to maintain the desired and distinguishing characteristics after propagation over several generations.

'Godiva', a yellow raspberry, produces a primocane crop which begins in August and continues until early November. The floricane crop begins in about mid May and continues until about July. Both the primocane and floricane yields (about 5.9 to 8.6 T/acre and about 8.6 to 12.5 T/acre, respectively) are high relative to other comparable cultivars. The fruit of the 'Godiva' raspberry plant is medium to large in size and remains consistently so throughout its harvest period. The fruit of 'Godiva' is normally light yellow in color when harvested but attains a deeper yellow color after harvest or when fully mature.

DETAILED DESCRIPTION OF THE PLANT

Figure 1:
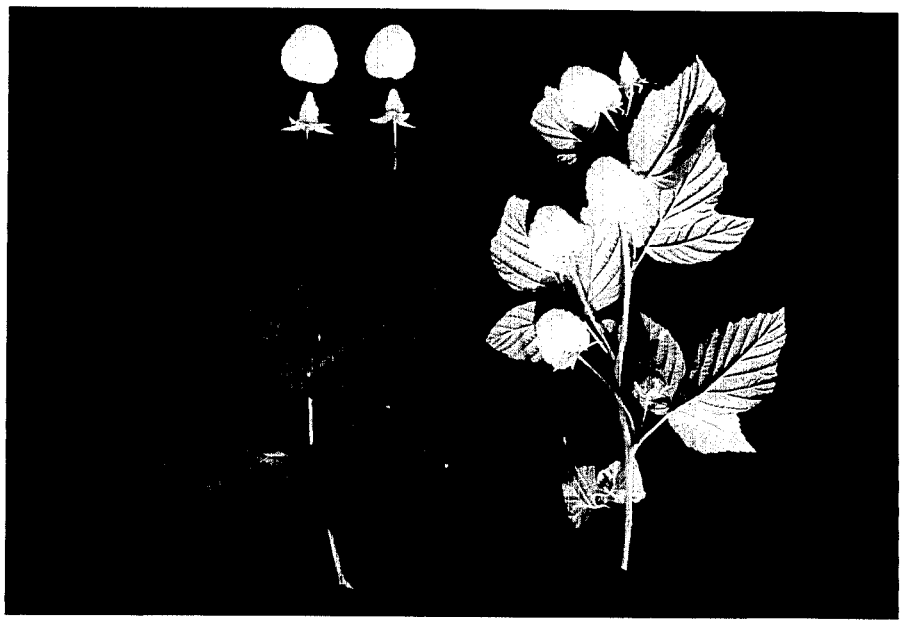
FIG. 1 is a color photograph of a 'Godiva' primocane mature leaf and fruiting shoot, showing various stages of fruit development.
Figure 2:
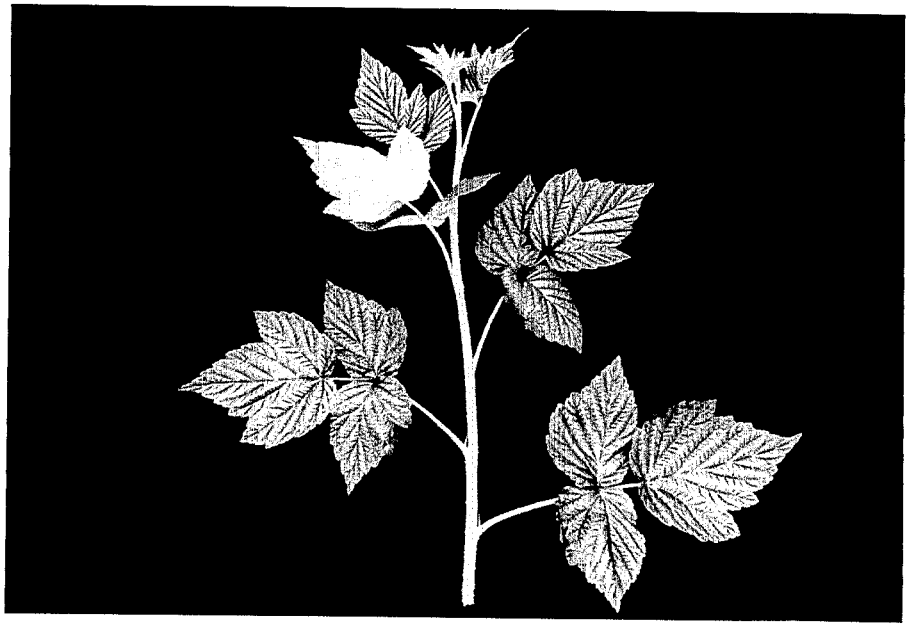
FIG. 2 is a color photograph of a 'Godiva' primocane shoot.

Throughout this specification, color names beginning with a small letter signify that the name of the color, as used in common speech, is aptly descriptive. Color names beginning with a capital letter designate color values based on the R.H.S. Colour Chart published by The Royal Horticultural Society of London, England.

The following description is a detailed description of the 'Godiva' raspberry cultivar and the fruit produced thereaby, as grown in Watsonville, Calif. between 1991 and 1994, and is believed to apply to plants of the 'Godiva' cultivar grown in similar conditions of soil and climate elsewhere.

The 'Godiva' fruit exhibits a light yellow color at harvest, but darkens after harvest to a deeper yellow. The fruit of the 'Godiva' plant is average in its ease of separation and of above average firmness at harvest. Post harvest fruit rot resistance is above average in comparison with many selections and cultivars.

The 'Godiva' cultivar has good resistance to late leaf rust. Resistance to powdery mildew and root rots is unknown. Cold tolerance of the new cultivar has not been established.

The new cultivar is particularly characterized and distinguished from other yellow fruited cultivars by its high yielding capacity on both primocane and floricane crops, and its excellent flavor. The 'Godiva' cultivar also has greater firmness than most other yellow fruited cultivars.

'Godiva' is distinguished from its seed parent, selection C96.7, by having greater firmness, a better flavor balance and higher yields. The new cultivar is distinguished from its pollen parent, selection F167.1, by having a higher yielding capacity.

Tables 1 and 2 present morphological information about the new 'Godiva' raspberry cultivar.

TABLE 1

PLANT CHARACTERISTICS OF 'Godiva'

| | |
|---|---|
| General | |
| Plant size: | large |
| Growth habit: | upright; erect |
| Density of foliage: | medium |
| Productivity: | productive |
| Self fruitfulness: | self fruitful |
| Primocane fruiting: | |
| percent of cane length flowering as primocane: | about 30% |
| percent of total yield from primocane crop: | about 30–45% |
| Suckering tendency: | medium |
| Utility of fruit: | fresh market shipping |

TABLE 1-continued

| PLANT CHARACTERISTICS OF 'Godiva' | |
|---|---|
| Canes | |
| Primocanes | |
| Number of fruiting laterals/cane: | about 13–20 |
| Number of canes/crown: | medium/about 4–15 |
| Young shoot pigmentation: | not present |
| Length: | about 69–87" |
| Diameter (end of 1st year): | |
| cane base: | about 0.44–0.66" |
| central ⅓ of cane: | about 0.41–0.56" |
| Depressions in cross section: | absent |
| Prickles: | |
| pigmentation: | lightly pigmented |
| density on young shoots: | medium |
| attitude of tip: | downward |
| size: | small |
| texture: | heavy |
| presence and | uniformly distributed |
| Pubescence on canes: | present |
| Internodal distance (at central ⅓ of cane): | about 1.3–2.3" |
| Lenticels: | not visually detectable |
| Floricanes | |
| Length: | about 40–70" |
| Number nodes/lateral branch (at mid cane): | about 7–13 |
| Number of flowers/node (at 4th node from apex on a mid cane lateral): | about 1–3 |
| Leaves | |
| Arrangement: | compound |
| Relief between veins: | medium |
| Leaflet number: | 3–5, usually 5 |
| Terminal leaflet: | |
| length: | about 3.9–5.9" |
| width: | about 2.9–4.9" |
| shape: | ; often lobed |
| tip: | acute to acuminate |
| base: | cordate |
| margin: | doubly serrate |
| Lateral leaflets (basal pair): | |
| overlap: | overlapping |
| orientation: | opposite |
| shape: | oblique |
| tip: | acute |
| base: | oblique |
| margin: | doubly serrate |
| length: | about 3.7–4.3" |
| width: | about 2.6–3.3" |
| Rachis length between terminal leaflet and adjacent lateral leaflets: | about 0.68–1.8" |
| Color: | |
| face: | Green 137A |
| underside: | Green 191A |
| Petiole: | |
| length: | about 2.9–5.4" |
| pigmentation of upper surface: | absent |
| pigmentation of underside: | absent |
| Stipule orientation: | erect |
| Flowers | |
| Flowering period: | |
| primocane: | early July to mid September |
| floricane: | late March to early June |
| Petal: | |
| color: | White 155B |
| length: | about 0.18–0.25" |
| width: | 0.09–0.13" |
| number: | 5 |
| arrangement: | free |
| Pedicel coloration: | absent |

TABLE 2

| FRUIT CHARACTERISTICS OF 'Godiva' | |
|---|---|
| Fruit | |
| Harvest season: | |
| primocane: | begins early to mid August; ends early November |
| floricane: | begins mid May; ends early July |
| Color: | |
| immature: | Yellow 10C–10D |
| maturing: | Yellow-Orange 16B–16C |
| mature: | Yellow-Orange 21D |
| Dimensions: | |
| weight: | |
| primocane harvest | about 2.2–4.0 g (3.1 g mean) |
| floricane harvest: | about 2.3–4.1 g (3.1 g mean) |
| length (primocane): | about 0.62–0.78" |
| width (primocane): | about 0.56–0.75" |
| Soluble solids (%): | about 11.4% |
| Titratable acidity (% as citric acid): | about 2.0% |
| Seeds (weight): | about 1.4 mg |
| Number drupelets/fruit: | about 38–78 (57 mean) |

Figure 3:
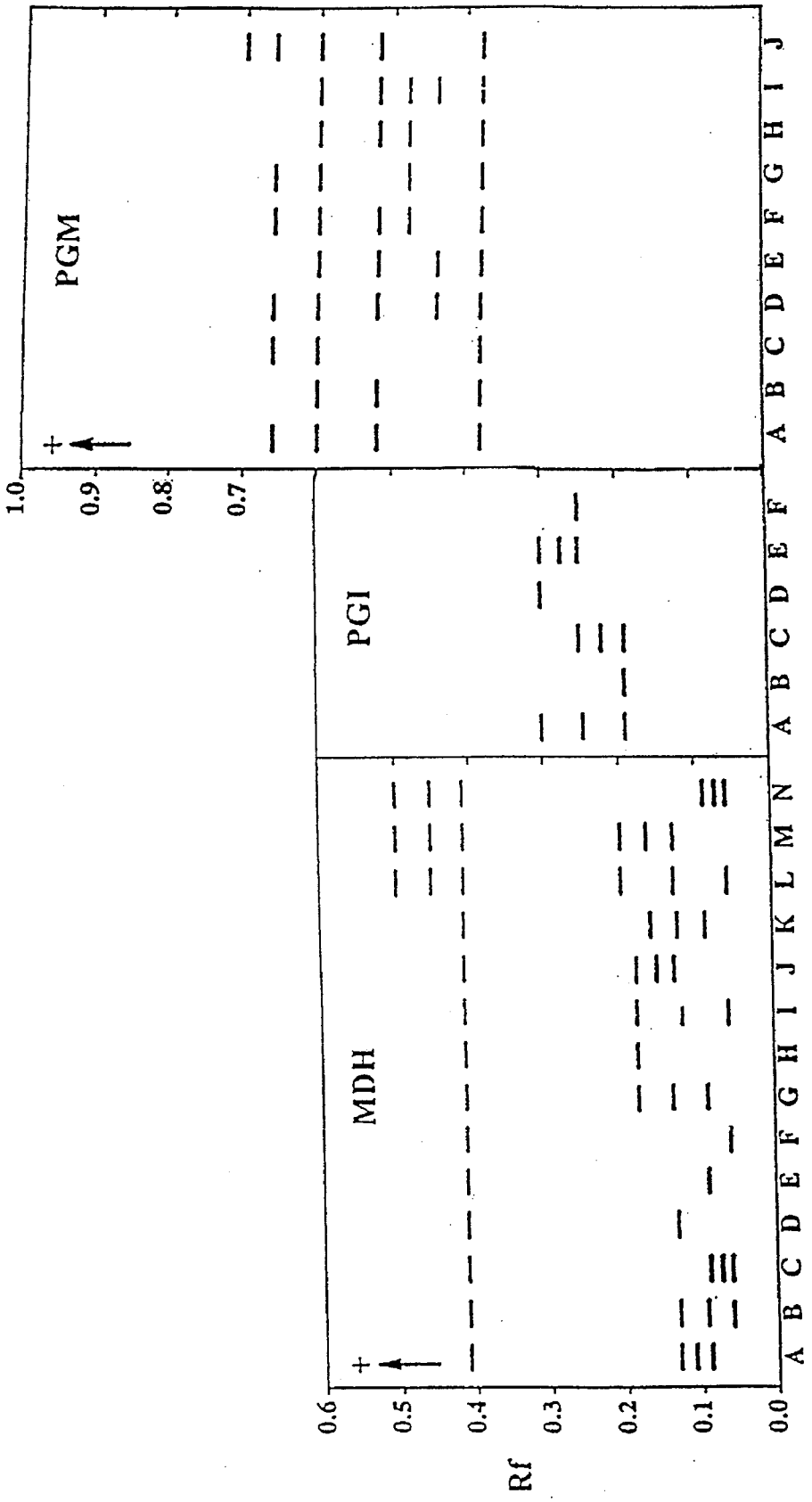
FIG. 3 is an interpretative drawing showing the cultivar banding patterns for the enzymes, MDH (malate dehydrogenase), PGI (Phosphoglucoisomerase) and PGM (phosphoglucomutase).

In addition to the foregoing morphological description, and to provide further means for identifying the new cultivar and distinguishing it from some other somewhat similar and/or related raspberry cultivars, the new 'Godiva' cultivar has been analyzed to obtain an indication of its genetic makeup. Specifically, leaves of the 'Godiva', 'Hollins' (U.S. Plant Pat. No. 8,027), 'Summit' (unpatented), 'Isabel' (U.S. Plant patent applied for), 'Sweetbriar' (U.S. Plant Pat. No. 4,486), 'Joe Mello' (U.S. Plant Pat. No. 6,493) and 'Wilhelm' (U.S. Plant patent applied for) cultivars were electrophoretically analyzed, the patterns designated and procedures utilized being per those described by J. C. Cousineau and D. J. Donnelly, "Use of Isoenzyme Analysis to Characterize Raspberry Cultivars and Detect Cultivar Mislabeling," *HortScience,* vol. 27 (9):1023–1025 (1992). The results of the electrophoreses analysis are presented in Table 3 below, the letters representing the cultivar banding patterns for each enzyme as shown in FIG. 3, taken from the above article.

TABLE 3

ISOZYME BANDING PATTERNS OF 'Godiva' COMPARED WITH 'Hollins', 'Summit', 'Isabel', 'Sweetbriar', 'Joe Mello' AND 'Wilheim'

| Cultivar | Isozyme | | |
|---|---|---|---|
| | PGI | MDH | PGM |
| 'Godiva' | B | A | D |
| 'Hollins' | D | E | D |
| 'Summit' | A | C | B |
| 'Isabel' | A | E | C |
| 'Sweetbriar' | D | D | A |
| 'Joe Mello' | D | E | C |

TABLE 3-continued

ISOZYME BANDING PATTERNS OF 'Godiva' COMPARED WITH 'Hollins', 'Summit', 'Isabel', 'Sweetbriar', 'Joe Mello' AND 'Wilheim'

| Cultivar | Isozyme | | |
|---|---|---|---|
| | PGI | MDH | PGM |
| 'Wilhelm' | D | A | C |

I claim:

1. A new and distinct cultivar of raspberry plant named 'Godiva' as herein illustrated and described.

* * * * *

UNITED STATES PATENT AND TRADEMARK OFFICE

CERTIFICATE OF CORRECTION

PATENT NO. : Plant 9, 696

DATED : November 19, 1996

INVENTOR(S) : Carlos D. Fear

It is certified that error appears in the above-indentified patent and that said Letters Patent is hereby corrected as shown below:

Column 2, Line 5: "thereaby" should read --thereby--;

Column 3, Line 21: "presence and" should read --presence and distribution on petioles--; and Column 3, line 40: "; often lobed" should read --ovate to cordate; often lobed--.

Signed and Sealed this

Seventeenth Day of June, 1997

*Attest:*

*Attesting Officer*

BRUCE LEHMAN

*Commissioner of Patents and Trademarks*